(12) United States Patent
Olson

(10) Patent No.: US 8,353,867 B2
(45) Date of Patent: Jan. 15, 2013

(54) MEDICAL DEVICES

(75) Inventor: Greg Olson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1677 days.

(21) Appl. No.: 10/838,540

(22) Filed: May 4, 2004

(65) Prior Publication Data

US 2005/0251107 A1    Nov. 10, 2005

(51) Int. Cl.
*A61M 37/00*    (2006.01)
*A61M 31/00*    (2006.01)

(52) U.S. Cl. .................................. 604/103.06

(58) Field of Classification Search ............... 604/96.01, 604/97.01, 99.01, 103.06–103.09, 108
See application file for complete search history.

(56) References Cited

U.S. PATENT DOCUMENTS

| | | | |
|---|---|---|---|
| 3,752,617 A | 8/1973 | Burlis et al. | |
| 4,795,439 A * | 1/1989 | Guest | 604/43 |
| 4,963,313 A | 10/1990 | Noddin et al. | |
| 5,195,969 A | 3/1993 | Wang et al. | |
| 5,248,305 A | 9/1993 | Zdrahala | |
| 5,270,086 A | 12/1993 | Hamlin | |
| 5,525,388 A | 6/1996 | Wand et al. | |
| 5,614,136 A * | 3/1997 | Pepin et al. | 264/40.3 |
| 5,639,409 A | 6/1997 | Van Muiden | |
| 5,714,110 A | 2/1998 | Wang et al. | |
| 5,725,814 A | 3/1998 | Harris | |
| 5,807,520 A | 9/1998 | Wang et al. | |
| 5,820,594 A | 10/1998 | Fontirroche et al. | |
| 5,824,173 A | 10/1998 | Fontirroche et al. | |
| 6,027,477 A | 2/2000 | Kastenhofer | |
| 6,030,405 A | 2/2000 | Zarbatany et al. | |
| 6,045,547 A | 4/2000 | Ren et al. | |
| 6,120,364 A | 9/2000 | Laflamme | |
| 6,136,258 A | 10/2000 | Wang et al. | |
| 6,193,738 B1 | 2/2001 | Tomaschko et al. | |
| 6,319,228 B1 | 11/2001 | Kastenhofer | |
| 6,464,683 B1 | 10/2002 | Samuelson et al. | |
| 6,471,673 B1 | 10/2002 | Kastenhofer | |
| 6,488,694 B1 | 12/2002 | Lau et al. | |
| 6,503,224 B1 | 1/2003 | Forman et al. | |
| 6,554,841 B1 | 4/2003 | Yang | |
| 6,595,952 B2 | 7/2003 | Forsberg | |
| 6,663,614 B1 * | 12/2003 | Carter | 604/525 |
| 6,702,781 B1 | 3/2004 | Reifart et al. | |
| 7,128,862 B2 | 10/2006 | Wang | |

(Continued)

FOREIGN PATENT DOCUMENTS

WO    WO 01/32398    5/2001

OTHER PUBLICATIONS

U.S. Appl. No. 10/263,225, filed Oct. 2, 2002.

(Continued)

*Primary Examiner* — Nicholas Lucchesi
*Assistant Examiner* — Pritesh Patel
(74) *Attorney, Agent, or Firm* — Seager, Tufte & Wickhem, LLC

(57) ABSTRACT

Medical devices and methods of making medical devices are described. In some embodiments, a medical device includes a member having a first portion with a first wall thickness, and a second portion with a second wall thickness, wherein the first portion is circumferentially rotated.

17 Claims, 3 Drawing Sheets

U.S. PATENT DOCUMENTS

| | | |
|---|---|---|
| 2002/0165523 A1 | 11/2002 | Chin et al. |
| 2003/0050686 A1 | 3/2003 | Raeder-Devens et al. |
| 2003/0065355 A1 | 4/2003 | Weber |
| 2003/0093107 A1 | 5/2003 | Parsonage et al. |
| 2003/0163148 A1 | 8/2003 | Wang et al. |
| 2004/0073250 A1 | 4/2004 | Pederson, Jr. et al. |

OTHER PUBLICATIONS

U.S. Appl. No. 10/645,014, filed Aug. 31, 2003.
U.S. Appl. No. 10/645,055, filed Aug. 31, 2003.

* cited by examiner

MEDICAL DEVICES

TECHNICAL FIELD

The invention relates to medical devices, such as, for example, medical tubing, catheters, guidewires, and medical balloons.

BACKGROUND

Intravascular medical devices such as, for example, guide wires, catheters, and medical tubing, allow physicians to perform a medical procedure, such as balloon angioplasty or delivery of an endoprosthesis, e.g., a stent. In some cases, a device is inserted into a patient's vascular system at a convenient site and subsequently delivered, e.g., pushed, through the vascular system to a target site. The path that the device takes through the vascular system to the target site can be relatively tortuous, for example, requiring the device to change direction frequently.

In some circumstances, it is desirable for the device to have relatively good flexibility so that it can track along the tortuous path. At the same time, the device preferably has good pushability so that forces applied proximally to the device can be transmitted distally to deliver the device.

SUMMARY

The invention relates to medical devices. In one aspect, the invention features medical devices having one or more portions that are rotated, e.g., circumferentially rotated. The portion(s) can be, for examples, portions of decreased or increased thickness and/or diameter, relative to other portion(s) of the medical device. Imparting a rotation to the portion(s) can enhance the compression strength of the portion(s).

In another aspect, the invention features a medical device, including a member having a first portion with a first wall thickness, and a second portion with a second wall thickness different than the first wall thickness, the first portion being circumferentially rotated.

In another aspect, the invention features a medical device, including a member having a first portion with a first diameter, and a second portion with a second diameter different than the first diameter, the first portion being circumferentially rotated.

Embodiments of the above aspects of the invention may include one or more of the following features. The member is a tubular member. The first wall thickness is less than the second wall thickness. The second portion is substantially free of circumferential rotation. The first portion is tapered. The first portion has an inner diameter less than an inner diameter of the second portion. The first portion has an outer diameter less than an outer diameter of the second portion. The first portion has an inner diameter greater than an inner diameter of the second portion. The first portion has an outer diameter greater than an outer diameter of the second portion. The first portion has a compression strength greater than a compression strength of an identical first portion without circumferential rotation. The member comprises a polymer.

In another aspect, the invention features a method of making a medical device. The method includes changing a thickness of a first portion of an elongated member; rotating the first portion relative to a longitudinal axis of the member; and incorporating the member into the medical device.

In another aspect, the invention features a method of making a medical device, including changing a diameter of a first portion of an elongated member; rotating the first portion relative to a longitudinal axis of the member; and incorporating the member into the medical device.

In yet another aspect, the invention features a method of making a medical device including rotating a first portion of an elongated member relative to a longitudinal axis of the member, the first portion having a thickness different than a thickness of a second portion of the elongated member. The method can further include incorporating the member into the medical device.

In yet another aspect, the invention features a method of making a medical device including rotating a first portion of an elongated member relative to a longitudinal axis of the member, the first portion having a diameter different than a diameter of a second portion of the elongated member. The method can further include incorporating the member into the medical device.

Embodiments of the above aspects of the invention may include one or more of the following features. The thickness of the first portion is reduced, e.g., relative to the second portion. The method further includes decreasing an inner diameter or an outer diameter of the first portion, e.g., relative to the second portion. The method further includes increasing an inner diameter or an outer diameter of the first portion, e.g., relative to the second portion. The method further includes heating the first portion. The first portion is changed in thickness and rotated simultaneously. The elongated member is a tubular polymer member.

In another aspect, the invention features a method of making a medical device, including changing a thickness of a first portion of an elongated member from the first thickness to a second thickness; increasing the compression strength of the first portion relative to an identical first portion having the first thickness; and incorporating the member into the medical device.

Embodiments may include one or more of the following features. The second thickness is less than the first thickness. The method further includes changing a diameter of the first portion. The diameter is increased. The diameter is decreased. The diameter is an inner diameter. The diameter is an outer diameter.

In another aspect, the invention features a method of making a medical device, including changing a diameter of a first portion of an elongated member from the first diameter to a second diameter; increasing the compression strength of the first portion relative to an identical first portion having the first diameter; and incorporating the member into the medical device.

Embodiments may include one or more of the following features. The second diameter is greater than the first diameter. The second diameter is less than the first diameter. The first and second diameters are inner diameters. The first and second diameters are outer diameters.

The device described herein can be in the form of a catheter, a guidewire, a medical balloon, a sheath, or a balloon catheter, such as an over-the-wire balloon catheter, a rapid exchange balloon catheter, a single operator exchange catheter, or a cutting balloon catheter.

Other aspects, features and advantages of the invention will be apparent from the description of the preferred embodiments and from the claims.

DETAILED DESCRIPTION

In one aspect, the invention features medical devices having one or more portions that are rotated, e.g., circumferentially rotated. The portion(s) can be, for examples, portions of decreased or increased thickness and/or diameter, relative to other portion(s) of the medical device. Imparting a rotation to the portion(s) can enhance the kink or buckling resistance of the portion(s).

Figure 1:
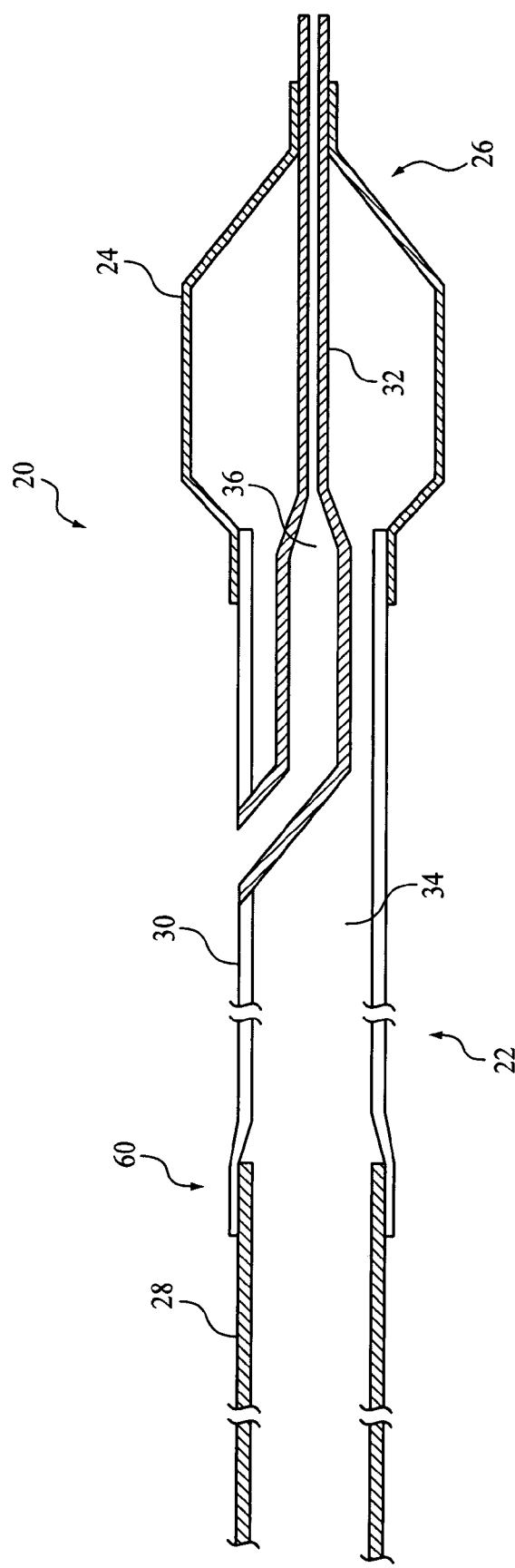
FIG. 1 is an illustration of a portion of a balloon catheter system, taken along a longitudinal cross section.

Referring to FIG. 1, a balloon catheter system 20 includes a catheter shaft 22 and an expandable balloon 24 carried by the catheter shaft at a distal portion 26. Catheter shaft 22 is formed of a plurality of tubular components or sections bonded (e.g., welded) together. As shown, catheter shaft 22 includes a proximal outer section 28, a distal outer section 30 bonded to the proximal outer section, and an inner section 32 bonded to the distal outer section. Proximal outer section 28 and distal outer section 30 define an inflation lumen 34, and inner section 32 defines a guidewire lumen 36. During use, balloon catheter system 20 can be delivered to a treatment site in the body by passing guidewire lumen 36 over a guidewire (not shown) emplaced in the body. At the treatment site, balloon 24 can be inflated or deflated by passing or withdrawing a fluid through inflation lumen 34 and into the interior of the balloon, e.g., to perform an angioplasty procedure or to deliver a stent. Examples of balloon catheters are described, for example, in U.S. Pat. Nos. 6,702,781 and 6,488,694; and exemplified by the Monorail™ family of balloon catheters (Boston Scientific-SciMed, Maple Grove, Minn.).

Figure 2A:
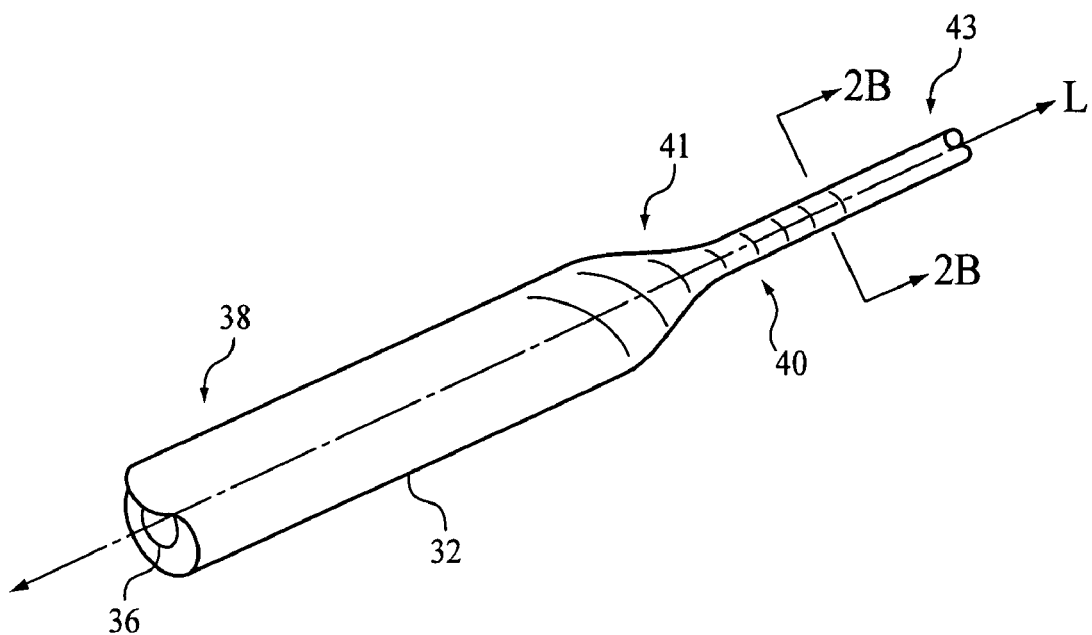
FIG. 2A is a perspective illustration of an inner section.
Figure 2B:
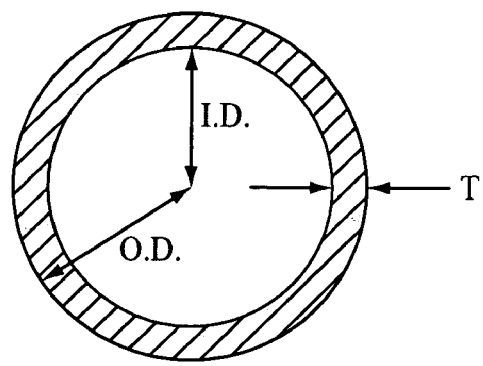
FIG. 2B is cross-sectional view of the inner section of the FIG. 2A, taken along line 2B-2B.

Referring also to FIGS. 2A and 2B, inner section 32 includes a proximal portion 38 and a distal portion 40 having a wall thickness (T), an inner diameter (ID) and an outer diameter (OD) that are reduced relative to the thickness and diameters of proximal portion 38. As shown, distal portion 40 has a tapered region 41 and a region 43 having a substantially constant cross-sectional profile. Both tapered region 41 and region 43 have reduced wall thickness and diameters relative to those of proximal portion 38. The reduced wall thickness and diameters of distal portion 40 decrease the cross-sectional profile of inner section 32, and decrease the cross-sectional profile of distal portion 26 of catheter system 20. As a result, the flexibility of distal portion 26 is enhanced, which allows catheter system 20 to better navigate or track a tortuous path. The reduced cross-sectional profile also allows catheter system 20 to access relatively narrow treatment sites.

In addition, still referring to FIGS. 2A and 2B, distal portion 40 of inner section 32 is circumferentially rotated to enhance the compression strength of the distal portion. In some embodiments, reducing the wall thickness and/or diameter(s) of inner section 32, sometimes called "necking", can reduce the radial strength of the inner section. By circumferentially rotating or twisting distal portion 40 such that the material of the distal portion has a degree of angular alignment, the compression strength and/or radial strength can be enhanced. During use, in which catheter system 20 is pushed to the treatment site, distal portion 40 that has been circumferentially rotated can better resist compression and/or collapse, which can lead to kinking or buckling of the catheter system.

The degree of circumferential rotation can vary along a selected portion. For example, one segment of distal portion 40 can be more rotated than another segment of the distal portion. Increasing the degree of rotation of a segment can increase its compression strength and/or radial strength, but decrease its flexibility. The amount of rotation can range from about 2 turns/inch to about 20 turns/inch. The rotation can be clockwise and/or counter-clockwise as viewed down the longitudinal axis. For example, one or more portions can be rotated clockwise, and one or more other portions can be rotated counterclockwise.

Figure 3:
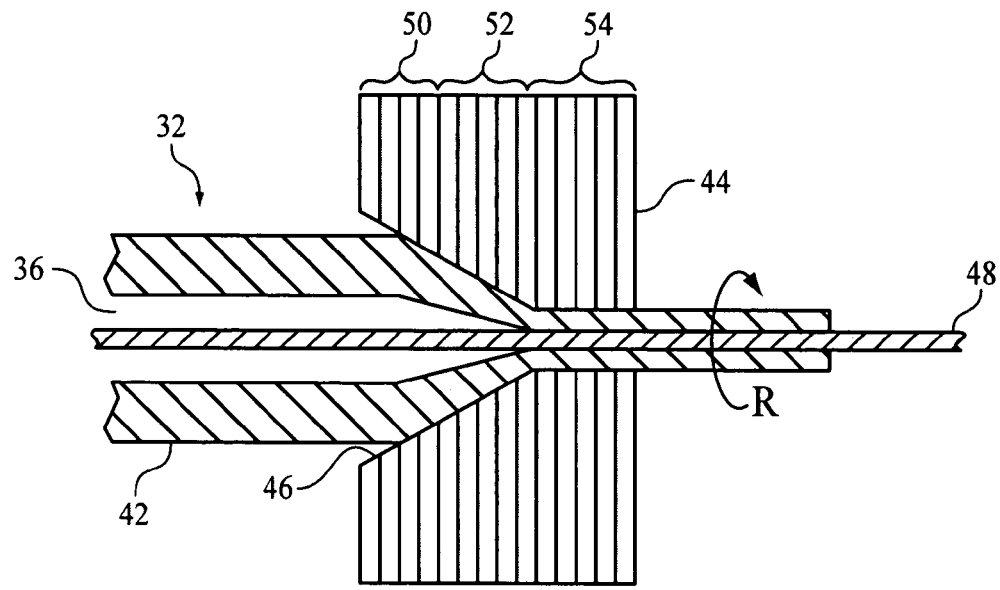
FIG. 3 is an illustration, taken along a longitudinal cross section, of a tube passing through a die.

Distal portion 40 of inner section 32 can be formed by passing a tube through an appropriately configured die and realigning the tube. Referring to FIG. 3, a tube 42 having generally the dimensions of proximal portion 38 is inserted into a heatable die 44 having an appropriately configured cavity 46, e.g., a conical or tapered cavity configured to form tapered region 41. As shown, a mandrel 48 is inserted into tube 42 to maintain the integrity of lumen 36. Die 44 and/or mandrel 48 is heated to a temperature sufficient to soften the material of tube 42 so that the tube becomes pliable and can be rotated. For example, tubes including Pebax™ polymers can be heated to about 341° F., tubes including nylon can be heated to about 330° F., tubes including polypropylene can be heated to about 273-300° F., and tubes including polyethylene (PE) can be heated to about 230° F. (low density PE) or about 260° F. (high density PE).

As tube 42 is inserted into die 44 and contacts cavity 46, the tube softens sufficiently so that its cross-sectional profile can be changed. As shown, the wall thickness, inner diameter and outer diameter of tube 42 is changed as the tube is passed through die 44. After tube 42 is passed to a predetermined point, tube 42 is circumferentially rotated about the longitudinal axis of the tube (arrow R) to impart a degree of angular alignment to the material of the tube. Subsequently, tube 42 is retracted from die 44 and incorporated into catheter system 20.

Other methods can also be used. Alternatively or additionally, die 44 can be rotated. For example, die 44 can be rotated in a first direction, and tube 42 can be rotated in an opposite rotation. Die 44 and tube 42 can be rotated in the same direction but at different speeds. In some embodiments, die 44 includes multiple heating zones, e.g., zones 50, 52, and 54, that are individually controllable. For example, one or more zones can be heated at a higher temperature than one or more other zones to effect more softening. The portion(s) of tube 42 that are more heated, and thus, more softened, can be more easily rotated relative to less heated portion(s) to yield a tube with variable angular alignment. Alternatively or in addition to using a heatable die, other heating sources can be used to heat tube 42. For example, tube 42 can be heated using infrared radiation or a heat gun.

In other embodiments, circumferential rotation can be applied to a member, such as a tubular member, having an increased inner diameter or an increased outer diameter. Referring again to FIG. 1, the proximal portion 60 of distal outer section 30, which is connected to proximal outer section 28, is enlarged or flared relative to other portions of the distal outer section. Proximal portion 60 can be circumferentially rotated or angularly aligned to enhance compression strength. The wall thickness of proximal portion 60 can be less than or equal to the wall thickness relative to other portions of distal outer section 30.

Figure 4:
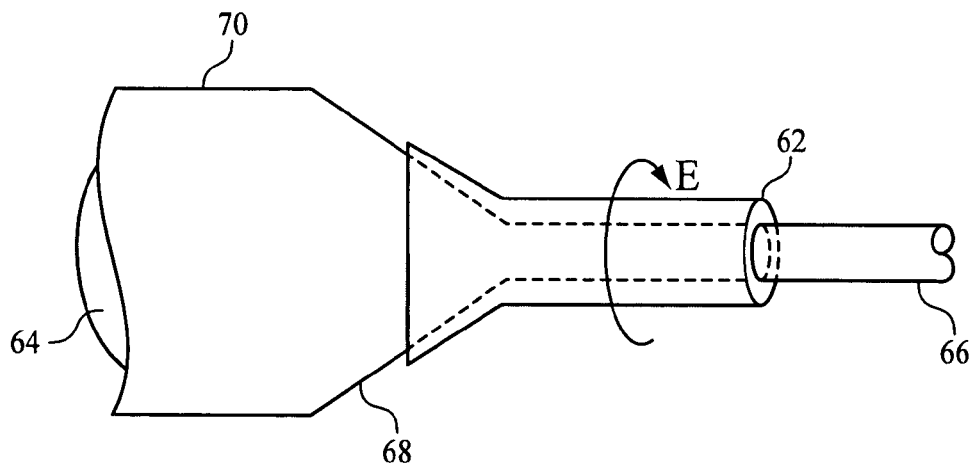
FIG. 4 is an illustration, taken along a longitudinal cross section, of a tube engaging with a die.

Flaring can be performed by inserting an appropriately shaped mandrel into a tube and realigning the tube. Referring to FIG. 4, a tube 62 having generally the dimensions of distal outer section 30 is passed over a heatable mandrel 64. Mandrel 64 has an elongated narrow portion 66, a flared or tapered portion 68, and a wide portion 70. Narrow portion 66 has an outer diameter substantially equal to the inner diameter of tube 62 to help maintain the integrity of the lumen of the tube. Mandrel 64 is heated to a temperature sufficient to soften the material of tube 62 so that the tube can be rotated.

Figure 5A:
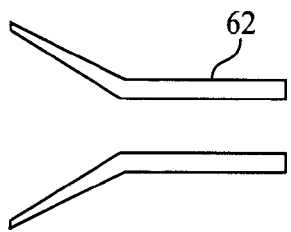
FIGS. 5A and 5B are longitudinal, cross-sectional views of tubes.
Figure 5B:
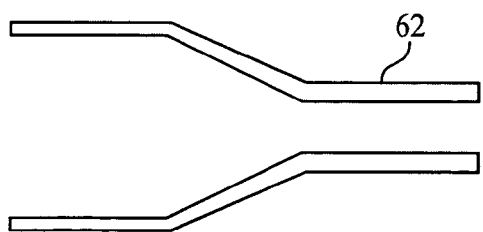

Similar to tube 42 and die 44 shown in FIG. 3, as tube 62 is passed over mandrel 64, the tube softens sufficiently so that its cross-sectional profile can be changed, e.g., increased. As shown, the wall thickness decreases, and the inner diameter and the outer diameter increase. After tube 62 is passed to a predetermined point, tube 62 is circumferentially rotated about the longitudinal axis of the tube (arrow E) to impart a degree of angular alignment to the tube. Subsequently, tube 62 is retracted from mandrel 64 and incorporated into catheter system 20. FIG. 5A shows a tube that can be formed if passed over flared portion 68, and FIG. 5B shows a tube that can be formed if passed over flared portion 68 and wide portion 70.

In some embodiments, mandrel 64, with or without tube 62, can be rotated. Mandrel 64 can have multiple, individually controllable heating zones, e.g., flared portion 68 and the portion of wide portion 70. Tube 62 can be heated with other heat sources, such as infrared radiation.

While FIG. 1 shows a particular type of balloon catheter system (sometimes called a "single operator exchange" balloon catheter), the circumferential rotation described herein can be applied to other balloon catheter systems. For example, the balloon catheter system can be an angioplasty balloon, an over-the-wire balloon catheter system, a rapid exchange balloon catheter system (e.g., as described in U.S. Pat. No. 6,702,781), or a cutting balloon system (e.g., as described in U.S. Publication US-2003-0163148-A1).

Furthermore, while the tubes described above are incorporated into a balloon catheter, the tubes can be sized and shaped to be incorporated in a variety of catheters. Examples of catheters include guide catheters (e.g., as described in U.S. Pat. No. 6,595,952), tumor ablation catheters, aneurysm catheters, urology catheters, and perfusion catheters (e.g., as described in U.S. Pat. No. 6,503,224).

The methods described herein can be used to make other medical devices. For example, multiple tubular segments of different compositions can be necked and/or flared, and joined together at their ends, e.g., by an overlapping bond, to form a guidewire, a tube, or a cannula. The proximal segments can be relatively stiffer than the distal segments to provide good pushability and trackability.

Similarly, multiple tubular segments can be joined together to form an introducer sheath or a restraining sheath for a stent delivery system, for example, as described in U.S. Pat. No. 6,488,694; and Raeder-Devens et al., U.S. 2003/0050686.

In other embodiments, the methods described herein can be used to manufacture a medical balloon. For example, referring again to FIG. 3, a first end of a balloon can be inserted into heatable die 44 to impart angular alignment to the tapered regions, or cones, of the balloon, and/or to the sleeve portions of the balloon. Subsequently, the second end of the balloon can be inserted into die 44 to impart angular alignment to the remaining tapered regions and/or sleeve portions. Die 44 can be modified to extend over the body portion of the balloon to impart angular alignment to the body portion. In some cases, during molding, the balloon wall in the body portion can be relatively thin to other portions of the balloon because of the relatively large amount of stretching.

Alternatively, angular alignment can be imparted to a tube, such as a co-extruded tube, and the tube can be formed into the medical balloon. For example, a tube can be prepared by an extrusion process. Generally, this process can involve the use of an extrusion apparatus (e.g., a crosshead, such as a compact crosshead) having a series of discs. A suitable extrusion apparatus, including some illustrative operating conditions, such as zone heating temperatures, polymer concentrations, feed rate, and line speed, are described in U.S. Ser. No. 09/798,749, entitled "Multilayer Medical Device" and filed on Mar. 2, 2001.

An exemplary system for controlling the feed rate or flow of polymers, including melt pumps, and systems and methods for controlling the pumps, is also described in WO 01/32398, entitled "Method and Apparatus for Extruding Catheter Tubing", hereby incorporated by reference in its entirety. Other methods include using servo-controlled valves, as described in Burlis et al., U.S. Pat. No. 3,752,617, hereby incorporated by reference.

Next, one or more selected portions of the tube corresponding to portion(s) of the balloon where angular alignment is desired is circumferentially rotated. For example, the lumen of the tube can be fitted with a supporting mandrel, and the selected portion(s) is heated and softened, e.g., by a heat gun. The tube can then be rotated relative to the mandrel to impart angular alignment.

To form a balloon, the formed (e.g., co-extruded and rotated) tube can be blow molded. In some embodiments, the tube is placed (e.g., centered) in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. The formed balloon can be heat treated, for example, to enhance folding memory, and/or folded into a predetermined profile.

Methods of forming a balloon from a tube are also described in, for example, commonly-assigned U.S. Ser. No. 10/263,225, filed Oct. 2, 2002, and entitled "Medical Balloon"; Anderson U.S. Pat. No. 6,120,364; Wang U.S. Pat. No. 5,714,110; and Noddin U.S. Pat. No. 4,963,313, all hereby incorporated by reference in their entirety.

In some embodiments, the components, such as tube 42, of the medical devices described above can include, for example, thermoplastics and thermosets. Examples of thermoplastics include polyolefins, polyamides, such as nylon 12, nylon 11, nylon 6/12, nylon 6, and nylon 66, polyesters (such as polyterephthalate (PET)), polyethers, polyurethanes, polyvinyls, polyacrylics, fluoropolymers, copolymers and block copolymers thereof, such as block copolymers of polyether and polyamide, e.g., Pebax®; and mixtures thereof. Examples of thermosets include elastomers such as EPDM, epichlorohydrin, polyureas, nitrile butadiene elastomers, silicones, etc. Thermosets, such as epoxies and isocyanates, can also be used. Biocompatible thermosets may also be used, and these include, for example, biodegradable polycaprolactone, poly(dimethylsiloxane) containing polyurethanes and ureas, and polysiloxanes. Other polymers are described in commonly assigned U.S. Ser. No. 10/645,055, filed Aug. 21, 2003. A component can include one or more polymers. The components can include a nanocomposite, as described in U.S. Patent Application Publication 2003/0093107.

The tubes and balloons described herein can include a plurality of layers, such as multiple coextruded layers. One or more layers can vary in thickness along the length of the tube or balloon. Multilayer tubes and balloons are described, for example, in commonly assigned U.S. Ser. No. 10/645,014, filed Aug. 21, 2003; and U.S. Ser. No. 10/645,055, filed Aug. 21, 2003.

In some embodiments, the tubes and balloons described herein can include one or more longitudinal stripes of a strengthening material, such as a liquid crystalline polymer. Medical components having longitudinal stripes are described in commonly assigned U.S. Patent Application Publication US-2003-0163148-A1.

In other embodiments, the components, such as tube 42, of the medical devices described above can include a non-polymer, such as a metal. For example, a metal tube can be heated to its softening point and circumferentially rotated as described herein. Examples of metals include stainless steel, gold, platinum, alloys containing molybdenum, alloys containing titanium (such as Nitinol), and alloys containing cobalt.

Other suitable balloon catheter systems are described in, for example, Wang U.S. Pat. No. 5,195,969; Hamlin U.S. Pat. No. 5,270,086; and exemplified by the Ranger® system available from Boston Scientific Scimed, Maple Grove, Minn.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. A balloon catheter, comprising:
   a balloon;
   a first tubular member disposed along a proximal portion of the balloon catheter, the first tubular member having an outer surface;
   a second tubular member disposed along a distal portion of the balloon catheter, the second tubular member having an inner surface;
   wherein the inner surface of the second tubular member overlaps with and is attached to the outer surface of the first tubular member; and
   a tubular inner member comprising a tubular proximal portion and a tubular distal portion,
   wherein the second tubular member and the inner member cooperate to define an inflation lumen fluidly connected to the balloon,
   wherein the tubular inner member has a proximal end coupled to the second tubular member, a distal end, and defines a guidewire lumen between the proximal end and the distal end,
   wherein the distal portion of the inner member is at least partially disposed in the balloon,
   wherein the proximal portion of the inner member has an inner diameter and wherein the distal portion of the inner member has an inner diameter that is less than the inner diameter of the proximal portion of the inner member, and
   wherein the distal portion of the inner member has been circumferentially rotated with respect to the proximal portion of the inner member to impart a degree of angular alignment to a material of the inner member.

2. The balloon catheter of claim 1, wherein the inner member comprises a tapered region between the proximal portion and the distal portion.

3. The balloon catheter of claim 2, wherein the tapered portion comprises a material with a degree of angular alignment.

4. The balloon catheter of claim 1, wherein the proximal portion of the inner member has a first wall thickness and the distal portion of the inner member has a second wall thickness that is less than the first wall thickness.

5. The balloon catheter of claim 1, wherein the distal portion of the inner member has a proximal end and a distal end and a length extending therebetween, and wherein the inner diameter of the distal portion of the inner member is constant along a majority of the length.

6. The balloon catheter of claim 1, wherein the inner member comprises a plurality of coextruded layers.

7. The balloon catheter of claim 1, wherein the proximal portion of the inner member is substantially free of circumferential rotation.

8. The balloon catheter of claim 1, wherein the proximal portion of the inner member has an outer diameter and wherein the distal portion of the inner member has an outer diameter that is less than the outer diameter of the proximal portion of the inner member.

9. A balloon catheter, comprising:
   a balloon;
   a first tubular member disposed along a proximal portion of the balloon catheter, the first tubular member having an outer surface;
   a second tubular member disposed along a distal portion of the balloon catheter, the second tubular member having an inner surface;
   wherein the outer surface of the first tubular member and the inner surface of the second tubular member are secured to with an overlapping bond; and
   a tubular inner member comprising a tubular proximal portion and a tubular distal portion,
   wherein the inner surface of the second tubular member and an outer surface of the inner member cooperate to define an inflation lumen fluidly connected to the balloon,
   wherein an inner surface of the tubular inner member defines a guidewire lumen,
   wherein the tubular inner member has a proximal end coupled to the second tubular member,
   wherein the distal portion of the inner member is at least partially disposed in the balloon,
   wherein the inner member tapers between the proximal portion of the inner member and the distal portion of the inner member.

10. The balloon catheter of claim 9, wherein a first portion of the inner member has been circumferentially rotated to impart a degree of angular alignment to a material of the inner member.

11. The balloon catheter of claim 10, wherein a second portion of the inner member is substantially free of circumferential rotation.

12. The balloon catheter of claim 11 wherein the second portion of the inner member is proximal the first portion of the inner member.

13. The balloon catheter of claim 9, wherein the proximal portion of the inner member has a first wall thickness and the distal portion of the inner member has a second wall thickness that is less than the first wall thickness.

14. The balloon catheter of claim 1, wherein the second tubular member is flared.

15. The balloon catheter of claim 1, wherein the second tubular member is circumferentially rotated.

16. The balloon catheter of claim 9, wherein the second tubular member is flared.

17. The balloon catheter of claim 9, wherein the second tubular member is circumferentially rotated.

* * * * *